United States Patent
Halverson

(10) Patent No.: US 8,426,210 B2
(45) Date of Patent: Apr. 23, 2013

(54) ANTIBODIES, SYSTEMS AND METHODS FOR DETERMINING RELATIVE HEMOLYTIC INDEX

(75) Inventor: Gregory R. Halverson, New York, NY (US)

(73) Assignee: New York Blood Center, Inc., New York, NY (US)

(*) Notice: Subject to any disclaimer, the term of this patent is extended or adjusted under 35 U.S.C. 154(b) by 279 days.

(21) Appl. No.: 12/908,770

(22) Filed: Oct. 20, 2010

(65) Prior Publication Data

US 2011/0091911 A1   Apr. 21, 2011

Related U.S. Application Data

(60) Provisional application No. 61/253,774, filed on Oct. 21, 2009.

(51) Int. Cl.
*G01N 33/72* (2006.01)

(52) U.S. Cl.
USPC ............. 436/67; 436/507; 436/513; 436/522; 436/811; 435/7.1; 435/7.25; 435/69.6

(58) Field of Classification Search ............ 436/507, 436/513, 517, 523, 522, 10, 69, 811, 67; 435/7.1, 7.2, 7.24, 7.25, 69.6, 334, 337
See application file for complete search history.

(56) References Cited

U.S. PATENT DOCUMENTS

2010/0261203 A1* 10/2010 Cicciarelli et al. ........... 435/7.21

OTHER PUBLICATIONS

Zupanska Assays to predict the clinical significance of blood group antibodies, Current Opinion in Hematology 5: 412-416 (1998).*
von Allmen et al. Development of a C1q-ABO-ELISA to measure C1q binding by human anti-A alloantibodies. J. Immunol. Methods 171 (1): 85-92(May 2, 1994).*
Arndt et al. "A retrospective analysis of the value of monocyte monolayer assay results for predicting the clinical significance of blood group alloantibodies." Transfusion, Sep. 2004, vol. 44, No. 9, pp. 1273-1281.
Fabron Jr. et al. "Application of noninvasive phagocytic cellular assays using autologous monocytes to assess red call alloantibodies in sickle cell patients." Transfusion and Aphereisis Science: Official Journal of the European Society for Haemapheresis, Aug. 2004, vol. 31, No. 1, pp. 29-35.
Schirmer et al. "Mouse models of IgG- and IgM-mediated hemolysis." Blood, vol. 109, No. 7, pp. 3099-3107, (Apr. 1, 2007).
Zupanska "Assays to predict the clinical significance of blood group antibodies." Current Opinion in Hemtaology, vol. 5, No. 6, Nov. 1998, pp. 412-416.

* cited by examiner

*Primary Examiner* — Gail R Gabel
(74) *Attorney, Agent, or Firm* — K&L Gates LLP; Louis C. Cullman; Michelle Glasky Bergman

(57) ABSTRACT

Disclosed herein are antibodies, systems and methods for assessing the risk of hemolysis following a blood transfusion with crossmatch incompatible blood. The disclosure provides a method for determining the relative hemolytic index and therefore the risk of post-transfusion hemolysis for said patient.

12 Claims, 5 Drawing Sheets

ANTIBODIES, SYSTEMS AND METHODS FOR DETERMINING RELATIVE HEMOLYTIC INDEX

RELATED APPLICATIONS

This application claims priority to U.S. Provisional Application No. 61/253,774, filed on Oct. 21, 2009, which is incorporated herein by reference in its entirety.

BACKGROUND OF THE INVENTION

One of the more serious issues in medical practice is the compatibility of blood transfusions between patients. Transfusion of incompatible blood can cause a hemolytic transfusion event also known as intravascular hemolysis.

Intravascular hemolysis consists of the destruction of red blood cells (RBCs) due to the rupture of the RBC membrane and the liberation of the cell's contents into the peripheral blood circulation. Free hemoglobin is observed in the plasma (hemoglobinemia) and urine (hemoglobinuria) and renal function is often impaired due to red cell membrane fragments blocking the renal tubules. If not treated quickly, this blockage can lead to the loss of renal function and death.

Hemolysis is triggered by activation of the immune system following a transfusion due to the presence of antibodies in the patient's blood that promote the attack of the transfused RBCs. In most blood-typing systems, individuals within a group do not carry the antibody for which the group is named. Accordingly, these patients should be able to receive blood from similarly typed individuals without triggering hemolysis. In some situations, however, individuals within a group can develop the antibodies that they are believed to lack. Such antibody development can occur following a previous blood transfusion, multiple pregnancies, certain infections or by natural exposure to proteins that are homologous to human blood group antigens. For example, studies have shown that approximately 1-2% of all transfused patients produce a specific alloantibody to a blood group antigen. These figures are much higher among multiply transfused patients, such as sickle cell anemia or leukemia patients, that develop an array of antibodies making the determination of blood transfusion compatibility much more difficult.

Every sensitized person who has produced an antibody that is considered to be clinically significant must receive cross-match-compatible blood. Cross-match compatibility is determined by mixing donor blood with the serum or plasma of the recipient and observing whether hemagglutination or hemolysis occurs. If either occurs, the blood is not transfused because of the possibility of causing a significant hemolytic event. Donor blood that is transfused must also be compatible with the recipient, and ideally shown to be antigen negative by testing with specific antisera. Thus, two tests are performed to increase the safety of the pending blood transfusion.

Presently available serologic tests can only identify the presence of RBC-specific antibodies in human sera. These assays cannot predict the probability of antibody-mediated hemolysis occurring during transfusion with any degree of certainty because they are not biologic assays.

The risk of a patient having a hemolytic event following transfusion is also evaluated partially based on historical data of that antibody specificity and what type of reaction it has been documented to cause. In very complex cases, a physician may have to weigh the consequences of transfusing incompatible blood with the survival of the recipient. Accordingly, improvement in blood compatibility testing is needed.

SUMMARY OF THE INVENTION

The disclosure provides new monoclonal antibodies, systems and methods to predict the likelihood of a hemolytic event following a blood transfusion. The described systems and methods are useful to determine the Relative Hemolytic Index ("RHI"). The disclosed systems and methods provide for a much more rapid, efficient and less expensive method for evaluation of the risk of intravascular hemolysis.

In one embodiment, A method of determining the risk of post-transfusion hemolysis in a blood transfusion recipient comprising the steps of: obtaining a sample of plasma or serum from a patient in need of a blood transfusion; determining the total immunoglobulin concentration in the plasma or serum or absorbed eluate of the sample; determining the antibody isotype of the immunoglobulins in the plasma or serum or absorbed eluate of the sample; determining the Fc gamma receptor affinity of the immunoglobulins in the plasma or serum or absorbed eluate of the sample; determining the C1q binding of the immunoglobulins in the plasma sample or serum or absorbed eluate of the sample; and calculating a relative hemolytic index and therefore the risk of post-transfusion hemolysis for said patient.

In certain embodiments, an RHI range of 30 or higher indicates a high (or significant) risk of intravascular hemolysis. In other embodiments, an RHI range of 15 to 30, or 15 or below indicates a moderate or low significant risk of intravascular hemolysis, respectively.

DETAILED DESCRIPTION OF THE INVENTION

The disclosure provides improved methods for determining the likelihood of intravascular hemolysis (i.e., the likelihood of RBC survival) following a blood transfusion. The disclosed methods are highly accurate as well as time and cost efficient.

The plasma molecules that promote hemolysis are referred to as immunoglobulins (Ig) or antibodies. Immunoglobulins are principally responsible for the detection and elimination of foreign antigens whether they are bacteria, toxins, proteins, carbohydrates or transfused cells. Once the immune system has responded to a particular antigen, any additional exposure to the same antigen causes a rapid secondary, or anamnestic response, resulting in a much higher titer of Igs in the serum.

Human Igs are classified into the following isotypes: IgG1, IgG2, IgG3, IgG4, IgA, secretory IgA, IgM, IgE and IgD. Immunoglobulin G (IgG) is by far the most prevalent serum antibody in normal human samples accounting for approximately 75% of the total mean serum Ig concentration.

The basic structure of the Ig molecule is two light chains, either δ (kappa) or λ (lambda), linked by disulfide bonds to two heavy chains of either of the 5 immunoglobulin classes (IgA, IgD, IgE, IgG and IgM) in the configuration of a monomer, dimer, trimer, quadrimer or pentamer. Each class differs in serum concentration, molecular weight, serum half life, ability to bind complement (a set of plasma proteins that act together to attack extracellular pathogens), active placental transfer, and binding properties to various proteins.

Certain Ig characteristics are known to increase the risk of hemolysis following transfusion. These characteristics include total Ig concentration, Ig isotype, and ability to bind C1q to activate complement and/or Fc gamma receptor (FcγR) affinity.

Figure 1:
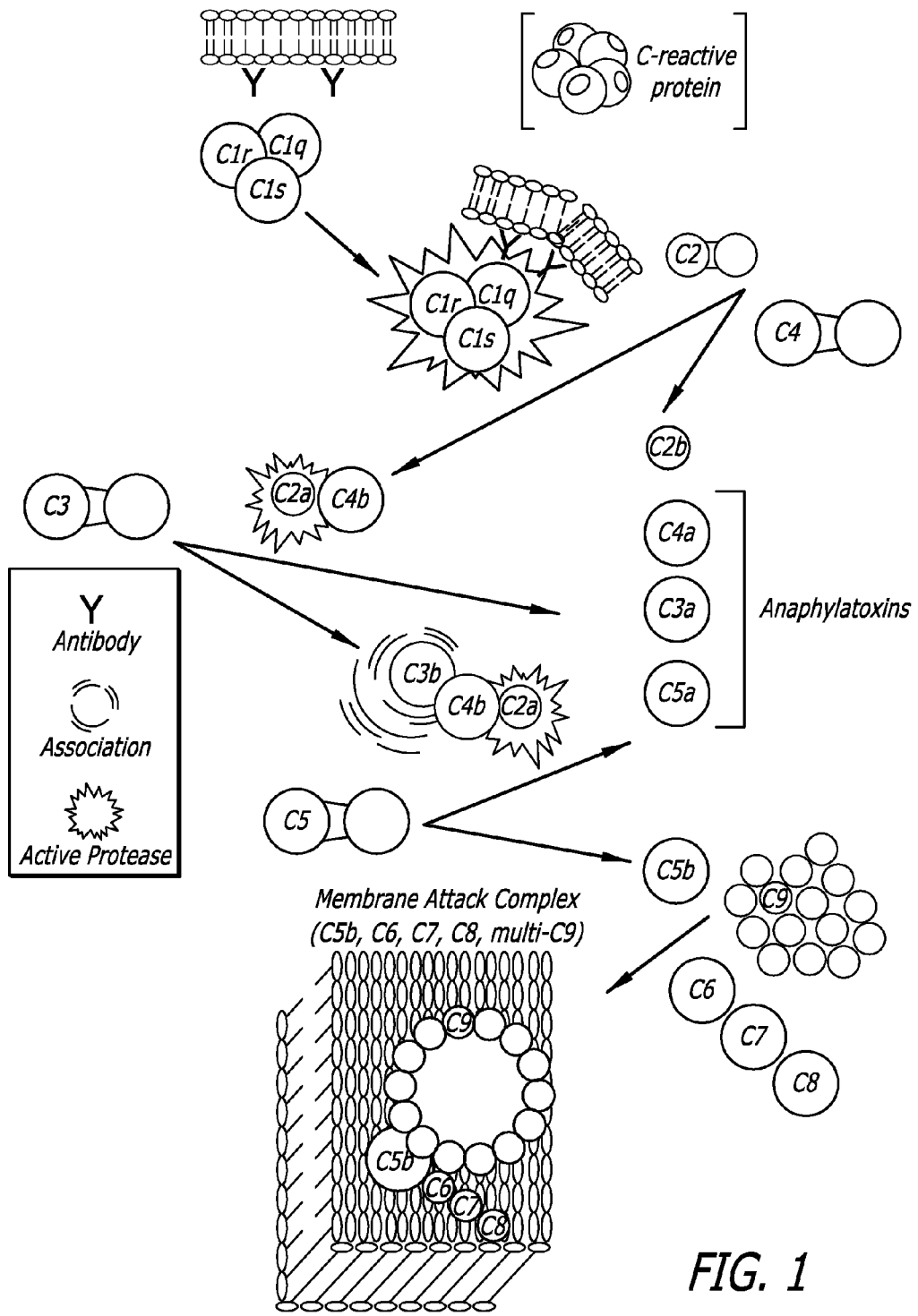
FIG. 1 depicts the complement activation pathway.
Figure 2:
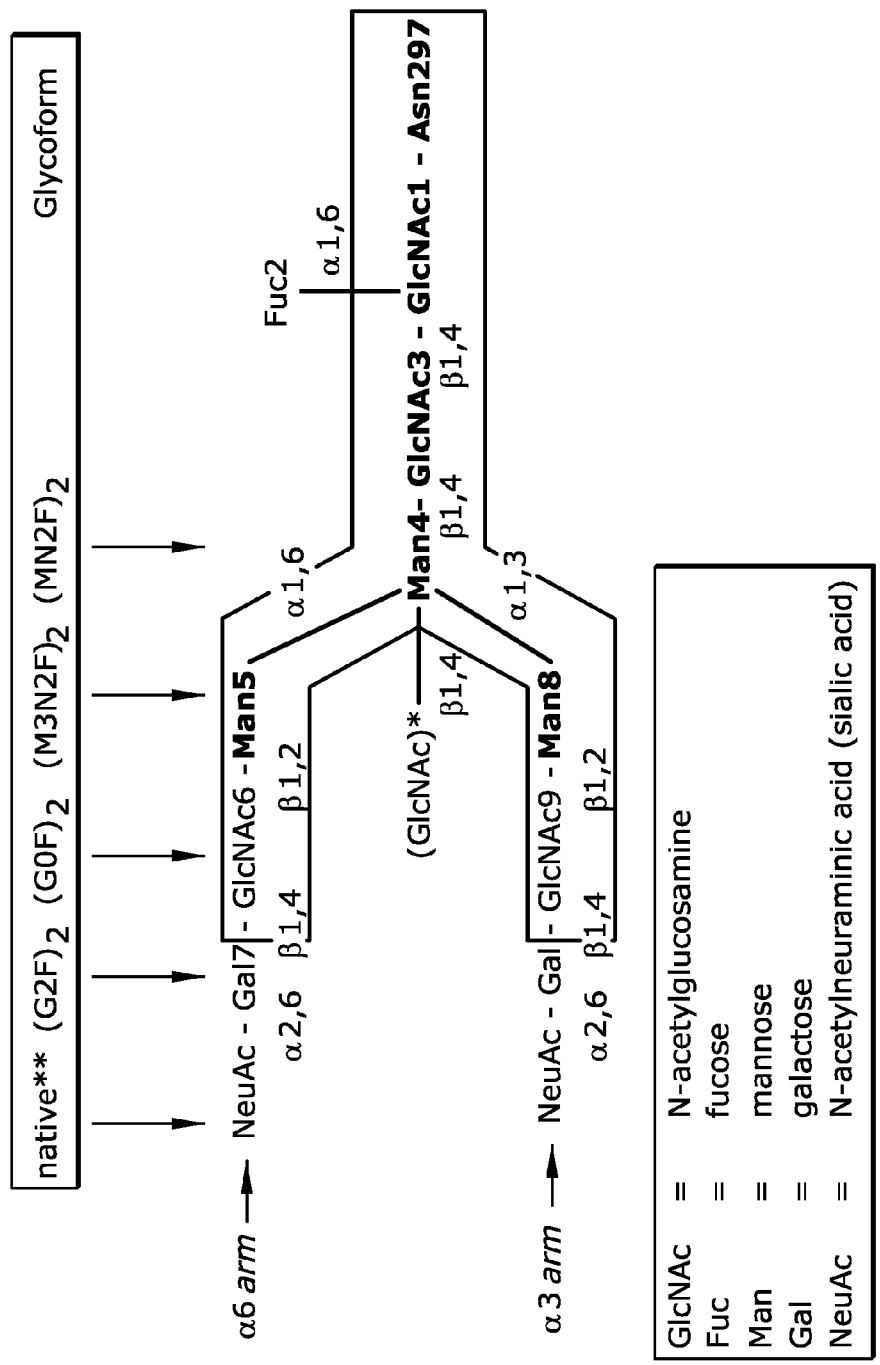
FIG. 2 depicts the carbohydrate sequence linked to Asn297 of human IgG1-Fc.

The classical pathway of complement activation (FIG. 1) starts with C1, a complex of serine proteases C1r and C1s (two each), and six larger C1q glycoproteins. Activation occurs by the binding of C1q to the Fc binding domains of IgG or IgM after they become attached to a target antigen. At least two of the N-terminal portions of C1q must be bound for C1 activation. It is the CH2 domain of the Fc receptor which is required for C1q binding. Three amino acid residues, Glu318, Lys320 and Lys322, have been found to be conserved in human IgG and in Igs from several other species, thus they have been designated as the C1q binding motif. However, further differences exist between the isotype core binding sites. The possibility exists, therefore, that these differences can determine the potential of an antibody, whether an alloantibody or an autoantibody, to cause decreased likelihood of transfused red cell survival or in vivo hemolysis.

The foregoing suggests that Igs efficient at binding C1q can more readily activate complement. It is known that IgM antibodies activate complement more efficiently than IgG antibodies. While isotypes IgG1, IgG2 and IgG3 can activate complement to varying degrees, IgG4 and IgA do not and thus are less likely to cause hemolysis.

Immunoglobulins binding FcγRs are also involved in the occurrence of hemolysis. Human FcγRs are expressed on the surface of immune cells (monocytes, macrophages, neutrophils, dendritic cells, NK cells, etc.). Each FcγR has different extracellular and intracellular domains, complicated by some having polymorphic extracellular domains. This includes high and low affinity members, all of which can bind to IgG immune complexes, but only high affinity receptors can bind to monomeric IgG. In humans, there is one high affinity receptor, FcγRI (CD64), and there are two families (FcγRII and FcγRIII) of low affinity IgG receptors comprising FcγRIIa (CD32a), FcγRIIb (CD32b), FcγRIIc (CD32c), FcγRIIIa (CD16a) and FcγRIIIb (CD16b). The term CD refers to cluster of differentiation or designation and refers to a specific antigen on a cell surface. FcRI, FcRIIa, FcRIIc and FcRIIIa are activating receptors. FcRIIb is an inhibitory receptor, and FcRIIIb is a GPI-linked receptor of uncertain function. FcγRI has three extracellular immunoglobulin (Ig)-like domains, one more domain than members of the FcγRII and FcγRIII families, thereby allowing direct activation by the binding of a monomeric antibody, rather than a complexed dimeric antibody such as with FcγRII and FcγRIII. FcγR binding initiates immune responses such as cytokine production, phagocytosis and serotonin release.

The glycosylation of the IgG antibody maintains the structure needed for C1q binding and FcγR affinity. It is thought that de-glycosylated IgG antibodies are unable to regulate in vivo activated inflammatory responses. Altered IgG glycosylation has been found in many auto-immune diseases such as rheumatoid arthritis and autoimmune thrombocytopenia where the antibodies are primarily de-glycosylated when compared to those from normal controls. The level of glycosylation has also been shown to vary with the process of aging and with immunization events, such as a blood transfusion and pregnancy. Accordingly, antibody glycosylation is a factor to consider in assessing the risk of hemolysis.

Figure 3A:
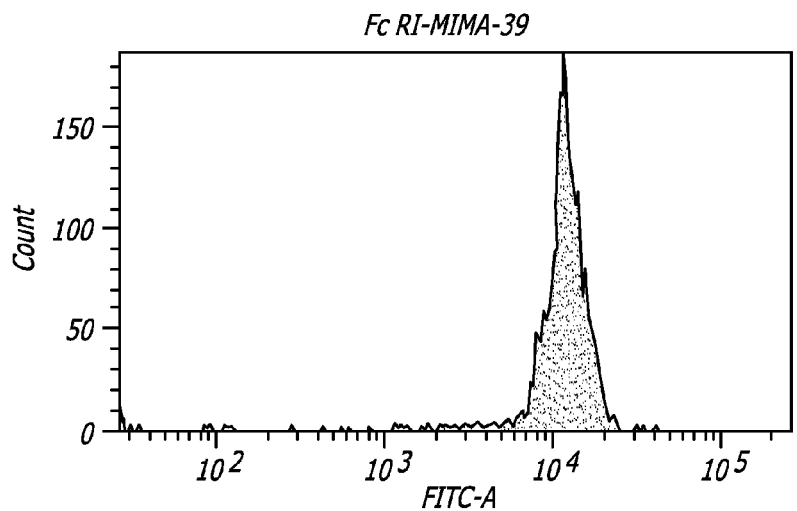
FIGS. 3A-C depicts the results Cytometric Bead assay assessment of Fc gamma receptor (FcγR) affinity of HIMA-39 for FCRI (A), FCRIIa (B), and FCRIIIa (C).
Figure 3B:
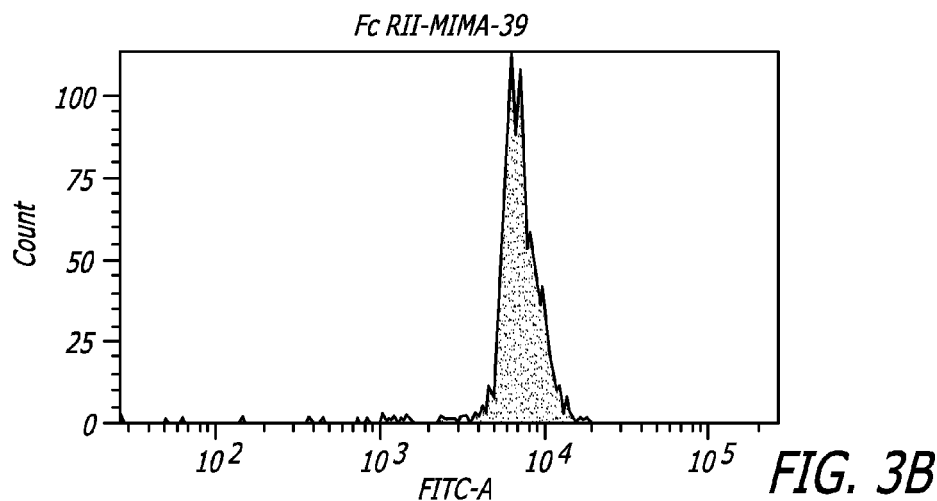
Figure 3C:
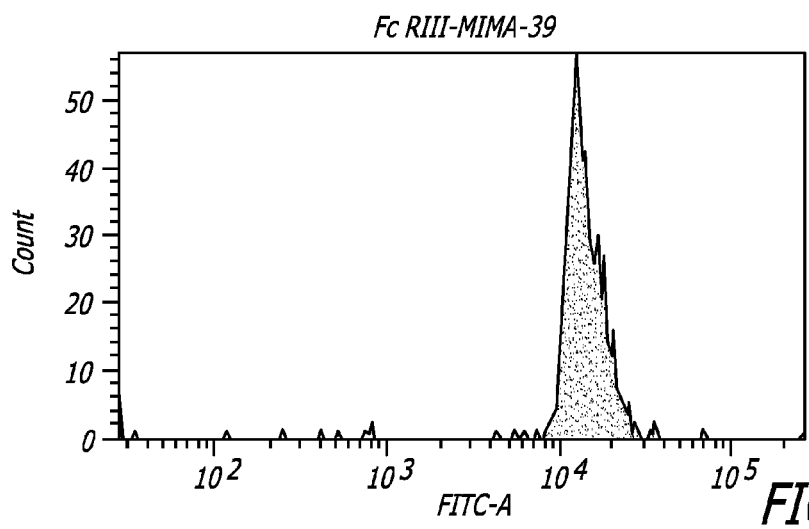
Figure 4A:
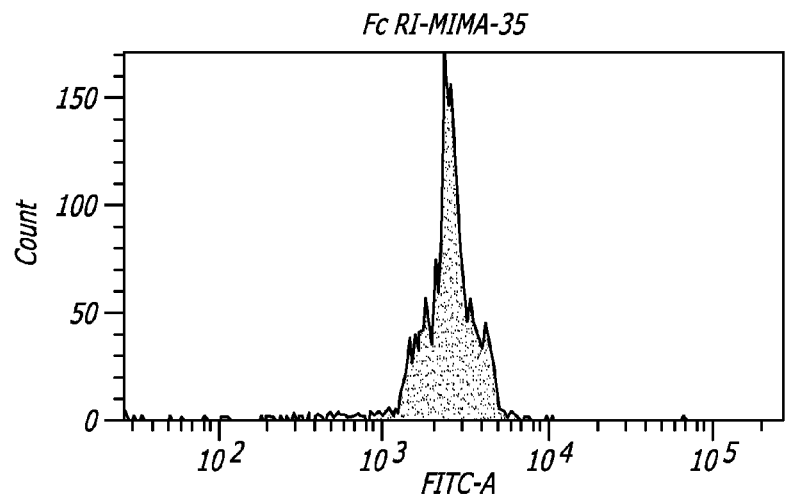
FIG. 4AC depicts the results Cytometric Bead assay assessment of Fc gamma receptor (FcγR) affinity of HIMA-35 for FCRI (A), FCRIIa (B), and FCRIIIa (C).
Figure 4B:
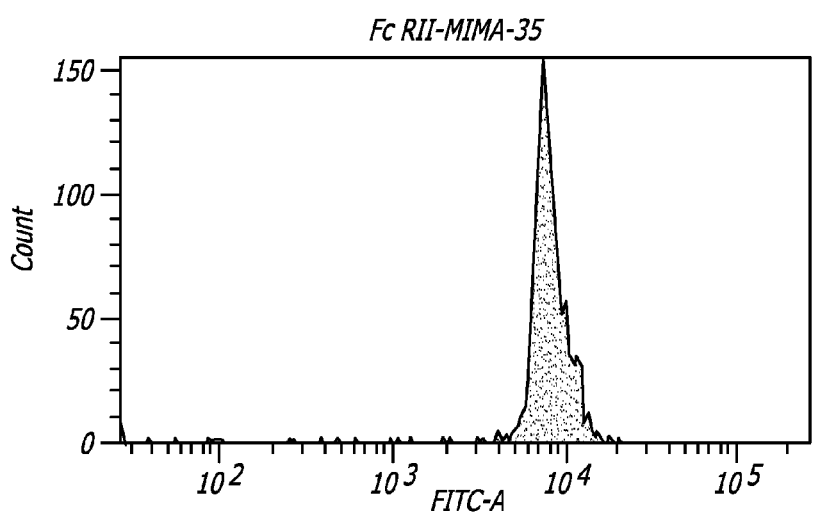
Figure 4C:
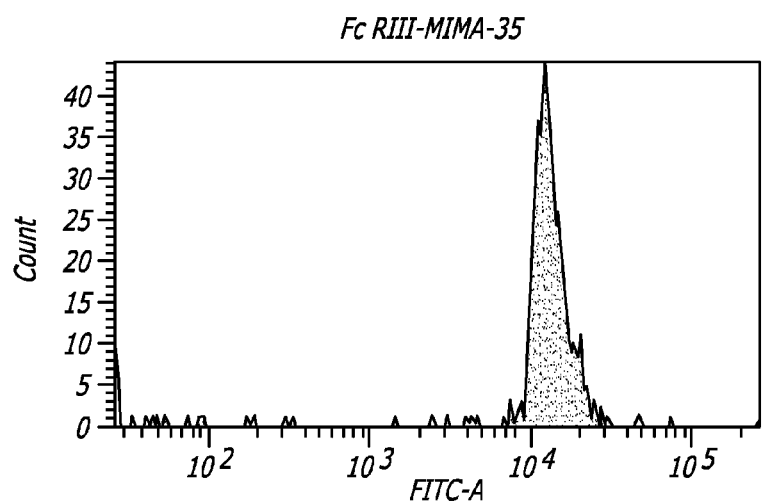

The N-linked glycan at Asn297 of the Fc receptor is alternatively glycosylated with fucose, galactose and terminal sialic acid at different time points. FIG. 3 depicts the carbohydrate sequence linked to Asn297 of human IgG1-Fc. The effects of alternative glycosylation can be determined by treating antibodies with PNGase F which cleaves between the innermost GlcNAc residue and the Asp297 residues of high mannose and complex oligosaccharides from the N-linked glycoproteins. Alternatively, treatment with neuraminidase can selectively hydrolyze α-(2->3), α-(2->6), α-(2->8) and/or α-(2-9) linked NeuAc residues from complex oligosaccharides, depending on the source of the terminal residues. De-glycosylated and de-sialylated antibodies can then be tested for altered binding activity to C1q and FcγRs.

The currently disclosed Relative Hemolytic Index (RHI) assay utilizes all of these factors in predicting the risk of hemolysis. Particularly, the RHI assay evaluates total IgG immunoglobulin concentration (or titer) and IgG/A/M isotype, the C1q complement binding capacity, and the FcγR affinity. By offering these tests in a multiplex assay, the RHI methods described herein can provide much needed laboratory data to predict a particular patient's RHI—that is, the likelihood for any particular patient antibody to cause a severe transfusion reaction, that is, decreased survival of transfused red cells and in vivo hemolysis. The described RHI methods also offer the following advantages: ability to use sample size as small as about 200 μL; ability to use hemolyzed samples; ability to use whole blood, serum or plasma on RBC elutions of each antibody; insensitivity to sample age; speed (i.e. several hours vs. several days); cost effectiveness; multiplex format; and accuracy.

Initially, two murine monoclonal antibodies, MIMA-211 and MIMA-212, which cause hemolysis by hemagglutination in the presence of fresh complement in vitro were produced. MIMA-211 and MIMA-212 both recognize determinants common to glycophorin A (GPA) and glycophorin B (GPB), which are prominently expressed on human RBCs. Because these antibodies caused hemolysis in vitro, they were used to standardize the described RHI testing methods to assess human antibodies.

Samples submitted for RHI evaluation can be serum, plasma, or an eluate, which is an absorbed and purified preparation of the antibody. MIMA-211 and MIMA-212 cause hemolysis by hemagglutination in vitro when fresh complement is added to the tests. In order to document that the elution procedure does not alter the glycosylation of an antibody, we prepared eluates of both MIMA-211 and MIMA-212 and tested them by hemagglutination with complement added. The eluates from both MIMA-211 and MIMA-212 caused in vitro hemolysis when fresh complement was present in the assay system, thus confirming that the elution process does not alter the glycosylation of the antibody.

Control antibodies MIMA-211 and MIMA-212 were then assayed in the Monocyte Monolayer Assay (MMA). The assay is generally performed as follows: mononuclear cells are washed in phosphate buffered saline, suspended in standard culture media containing 5% fetal calf serum, and added to tissue culture chamber slides. After 1 hour incubation at 37° C., the supernatant containing non-adherent cells is removed by pipette, then sensitized RBCs plus antigen positive or negative RBCs are added to the chambers with or without fresh normal sera as a source of complement. After 1 hour incubation at 37° C., the non-adherent RBCs are removed and the slides washed in PBS. The slides are then stained with Wright-Giemsa stain and observed microscopically for RBC adherence or engulfment. A cutoff of 5% monocyte reactivity, based upon the reactivity of unsensitized RBCs distinguishes between a positive and a negative assay.

The control murine antibodies produced significant MMA results of 12.3% and 23.3% with MIMA-211 and MIMA-212 respectively. The eluate results were 3.7% and 42% from MIMA-211 and MIMA-212 binding columns, respectively.

The Cytometric Bead Assay (CBA, BD BioSciences, Franklin Lakes, N.J.) is a flow cytometry analysis system which utilizes color-coded 7.5 μm polystyrene beads that can be covalently linked to water soluble proteins. Once functionalized, they act as a capture antigen for determination of the Total Ig in a serum sample as well as perform the IgG and IgM isotype in a single multiplex assay system. The advantage of using this method vs. ELISA, or other assays such as nephelometry, is that along with a very small sample size, it is also very sensitive, and much more rapid, only requiring approximately 4 hours for a complete sample analysis.

For C1q binding, ELISA plates (BD Falcon, Franklin Lakes, N.J.) were first coated with 10 ng purified C1q protein (Sigma, St. Louis, Mo.) and left overnight at 4° C. After blocking (SuperBlock, Pierce, Rockford Ill.) for two hours at room temperature (RT), the plates were washed twice (1% Tween-20 in PBS pH 7.3, Sigma) and 100 μl antibody added and incubated for 1 hour RT. After 3 washings, 100 μl HRP-conjugated anti-IgG was added and the plate again incubated for 1 hour. After 3 final washings, the color was developed by the addition of 50 μl TMB substrate with $H_2O_2$ and allowed to develop for 10 minutes. The reaction was then stopped by the addition of 50 μl 1N $H_2SO_4$ and the plate OD read at 450 nm. The results are shown below in Table 1 (total Ig Concentration, IgG/M Isotype and C1q Binding (IAT=Indirect Antiglobulin Test—the strength of hemagglutination scored from negative or 0 to a maximum positive of 12)).

levels indicate samples more likely to contain hemolytic antibodies. Samples with a generally lower Total IgG concentration did not produce a very strong signal for C1q binding.

Determination of FcγR binding affinity was accomplished using the Cytometric Bead Assay. For this testing, polystyrene beads were functionalized by covalently binding synthetic proteins corresponding to FcγRI (CD64), FcγRIIa (CD32), and FcγRIIIa (CD16). Confirmation of this conjugation was performed using murine anti-FcγR monoclonal antibodies. If the signal for the test sample was 500 MFI or greater than the signal for the negative control sample then the conjugation was successful. Through this process, it has been demonstrated that coating the beads with soluble protein is achievable.

Testing was conducted with the functionalized beads for FcγRI, FcγRIIa and FcγRIIIa to determine the affinity of our control monoclonal anti-Ds, HIMA-39 and HIMA-35 (see FIGS. 3A-C and 4A-C, respectively).

The described tests have been performed on many different types of antibodies and the same end result is nearly universally achieved. Although not necessary, a useful method of evaluating the effect of de-glycosylation or de-sialylation on antibody structure and function was determined and is provided herein as well. To examine the effect of de-glycosylation and/or de-sialylation of antibodies, antibody specimens were analyzed after being treated for 1 hour at 37° C. with 500 units of Peptide:N-Glycosidase F (PNGaseF) purified from *Flavobacterium meningosepticum* (New England BioLabs). Alternately, they were treated for 1 hour at 37° C. with 700 units of α-2,3/α-2,6 neuraminidase from *Clostridium perfringes* (Sigma Chemicals, St. Louis, Mo.). The monomeric composition of the de-glycosylated and de-sialylated preparations was confirmed by, in a non-limiting example, SDS-PAGE.

By removing the glycans attached to the Fc portion of the antibodies selected for assay, their activity in moderating the inflammatory response was assessed. Treatment with

TABLE 1

|  |  | Sample # | | | | | | | | | |
|---|---|---|---|---|---|---|---|---|---|---|---|
|  |  | 1 | 2 | 3 | 4 | 5 | 6 | 7 | 8 | 9 | 10 |
| IAT | score | 12 | 10 | 11 | 11 | 10 | 11 | 11 | 9 | 7 | 10 |
| Total IgG | ng/ml | 6667 | 1313 | 610 | 2668 | 100 | 7116 | 1287 | 1853 | 2368 | 1701 |
| IgG1 |  | 2031 | 310 | 398 | 1888 | 15 | 2771 | 221 | 893 | 763 | 398 |
| IgG2 |  | 2266 | 0 | 0 | 0 | 66 | 0 | 111 | 0 | 118 | 87 |
| IgG3 |  | 1026 | 53 | 50 | 235 | 41 | 608 | 144 | 179 | 467 | 46 |
| IgG4 |  | 27 | 0 | 0 | 0 | 2 | 0 | 11 | 0 | 0 | 0 |
| IgM |  | 0 | 0 | 0 | 0 | 0 | 0 | 0 | 0 | 0 | 0 |
| Total Sum |  | 5350 | 363 | 448 | 2123 | 124 | 3379 | 487 | 1072 | 1348 | 531 |
| C1q Binding Elisa Assay |  | POS | Neg | Neg | POS | Neg | Neg | Neg | POS | POS | Neg |
| Blank | .083 | .7319 | .1273 | .1377 | .6871 | .1393 | .1397 | .1289 | .5402 | .6778 | .1199 |
|  | .1377 | .7502 | .2998 | .2261 | .7779 | .1684 | .1954 | .1476 | .6227 | .6754 | .1423 |

The Total Sum of the isotypes (IgG1+IgG2+IgG3+IgG4) should be roughly equal to the Total IgG concentration. Without wishing to be bound by any particular theory, a possible reason that it is not in some of the results in Table 1 may be due to the fact that eluate samples were tested and this tends to concentrate the antibody in solution.

The results of the Total IgG and the isotype testing were compared to the results from the C1q binding by ELISA (Table 1). As can be seen in samples 1, 4, 8 and 9, these samples had higher IgG concentrations. These high IgG1

PNGase F, an amidase, specifically cleaves residues of mannose, hybrid and complex oligosaccharides from the N-linked glycoprotein. Treatment with neuraminidase (Sialydase) selectively de-sialylates the core structure of antibodies. Thus, these enzymes alter the structure of the antibody, changing its binding affinity.

HIMA-35 and HIMA-39 were subjected to the tests included in the RHI. The total Ig Concentration was determined along with the isotype, C1q binding and FcγR affinity.

The antibodies were also subjected to MMA to compare with results obtained with the RHI. Results are shown in Tables 2 and 3.

TABLE 2

| HIMA-39 | Test Result | Score |
|---|---|---|
| Titer | 1024 | 10 |
| Isotype | IgG1 | 10 |
| C1q Binding | 1.47 | 10 |
| FcγRI | High | 10 |
| FcγRIIa | High | 2 |
| FcγRIIIa | High | 5 |
| Total RHI |  | 47 |
| Interpretation |  | Significant |
| % MMA |  | 36% |

TABLE 3

| HIMA-35 | Test Result | Score |
|---|---|---|
| Titer | 1024 | 10 |
| Isotype | IgG1 | 10 |
| C1q Binding | 0.26 | 2 |
| FcγRI | Moderate | 10 |
| FcγRIIa | High | 2 |
| FcγRIIIa | High | 5 |
| Total RHI |  | 39 |
| Interpretation |  | Significant |
| % MMA |  | 38.7% |

Figure 5:
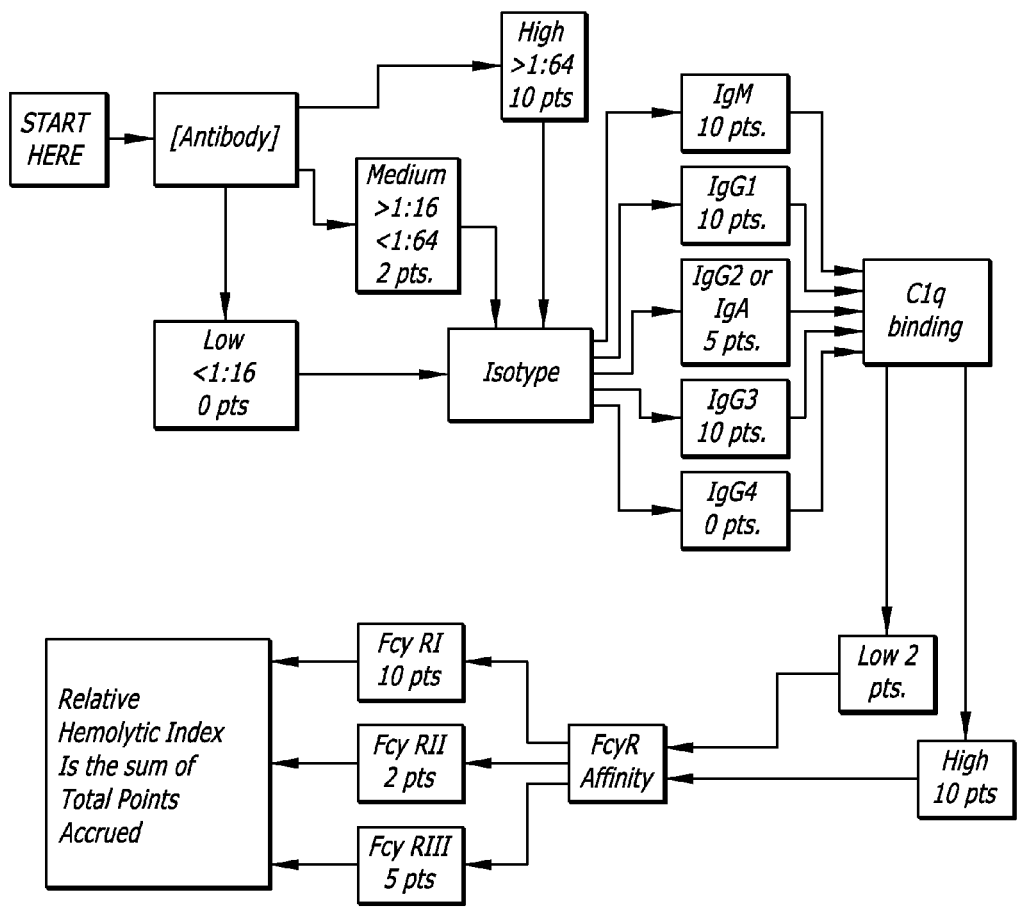
FIG. 5 is a flow chart of steps to establish a RHI score in accordance with an embodiment disclosed herein.

FIG. 5 provides a flow chart for the determination of the RHI as disclosed herein. In this example flow chart, if a sample is IgG4 of low titer, did not require C1q testing and did not have any FcγR affinity, the RHI is zero. However, if a sample is of a high titer IgG1, it would be further evaluated, and with a high C1q binding and FcγRI affinity, this sample achieved a RHI of 40, thus it is likely to cause in vivo hemolysis. Antibodies of high concentration and isotype IgG1, IgG2 and IgG3 with a high C1q binding affinity will predict a positive MMA. FcγR affinity to receptors I and IIIa provide additional evidence for in vivo antibody-mediated destruction of red cells.

15 or below and over 30 or higher. Greater than 30 is a high risk (or very significant) of reaction, while anything below 15 is considered to be low (very insignificant) risk of reaction. The RHI is calculated by the number of points each sample earns in the various tests. Adding the total points earned for Ig concentration, isotype presents (or predominant), C1q binding capacity (high or low) and affinity for each Fc gamma receptor on immune cells (I, IIa, IIIa) provides the score for the RHI.

In order to practice the methods disclosed herein, all that is required is the ability to decipher different wavelength emissions simultaneously over a light or infrared spectrum visible to the machine being used. Particular embodiments disclosed herein describe the use of a Cytometric Bead Assay to determine the Total Immunoglobulin concentration, the antibody isotype, and the Fc gamma receptor affinity. The set of tests done in multiplex format (Cytometric Bead Array) establish the Relative Hemolytic Index (RHI) for any particular antibody to cause in vivo hemolysis if transfusions were to be done. Although Cytometric Bead Array is utilized in certain embodiments, other arrays and assays can be used and are well within the skill of the art. Other possible platforms for determining the RHI include the Alpha-lisa method (Perkin Elmer, Norwalk Conn.), the Meso Scale Devices (Biacore, Piscataway N.J.), and any quantitative elisa assay (Sigma, St. Louis, Bio-Rad, Hercules, Calif., Pierce, Rockford Ill.) once the proper range of each test supernatant is determined.

By establishing newer methods for the study of immunoglobulins, namely as risk assessment tool in multiplex format, the RHI has been developed to predict transfusion-associated hemolysis. The RHI replaces the standard bioassays which are currently used, the chemoluminescence test, the antibody dependant cellular cytotoxicity assay (ADCC) the monocyte monolayer assay (MMA), and Cr51 RBC survival studies. The RHI is designed to be both a cost and time efficient tool for patient transfusion management. This test can be offered to the clinician who is worried about patient morbidity in the setting of incompatible blood transfusions due either to allo- or auto-antibodies. Including sample preparation, the RHI analysis can be completed within about 4 to about 6 hours, in contrast to the existing bioassays that require special skills, equipment and planning often takes days or even weeks to obtain results.

TABLE 4

| RHI Assay | Mab Anti-D 7E11 | RHI Score | Mab Anti-D 10D6 | RHI Score | Human Anti-c | RHI Score | Human Anti-D + C | RHI Score | Human Warm/Cold Mixed Auto | RHI Score |
|---|---|---|---|---|---|---|---|---|---|---|
| Total IgG | 1:1024 | 10 | 1:1024 | 10 | 1:2 | 0 | 1:2048 | 10 | 1:64 | 2 |
| IgG Isotype | IgG1 | 10 | IgG1 | 10 | IgG1 | 10 | IgG1 | 10 | IgG1 | 10 |
|  | IgG2 |  | IgG2 |  | IgG2 | 5 | IgG2 | 5 | IgG2 | 0 |
|  | IgG3 |  | IgG3 |  | IgG3 |  | IgG3 | 10 | IgG3 | 10 |
|  | IgG4 |  | IgG4 |  | IgG4 | 0 | IgG4 | 0 | IgG4 | 0 |
|  | IgM |  | IgM |  | IgM |  | IgM |  | IgM | 10 |
| C1q Binding | 0.26 | 2 | 1.47 | 10 | 0.68 | 10 | 0.54 | 10 | 0.38 | 2 |
| Fc gamma Receptor Affinity | I | 10 | I | 10 | I | 0 | I | 10 | I | 10 |
|  | IIa | 2 | IIa | 2 | IIa | 2 | IIa | 2 | IIa | 2 |
|  | IIIa | 5 | IIIa | 5 | IIIa | 0 | IIIa | 0 | IIIa | 0 |
| Total RHI* | 39 |  | 47 |  | 27 |  | 57 |  | 46 |  |
| Interpretation | Significant |  | Significant |  | Not Significant |  | Significant |  | Significant |  |
| % MMA** | 30.5% |  | 44% |  | 0.25% |  | 47.5% |  | 12.2% |  |

*RHI over 35 considered significant
**Total MMA over 5% considered significant

The % MMA cutoff value of 5% has been shown to indicate the probability of a significant reaction due to the presence of antibodies to RBC antigens. The range for the RHI is between Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of determining the risk of post-transfusion hemolysis in a blood transfusion recipient by determining a relative hemolytic index for said recipient, the method comprising the steps of:

obtaining a sample of plasma or serum from a patient in need of a blood transfusion;

optionally preparing an absorbed eluate of the sample;

measuring the total immunoglobulin concentration in the sample or absorbed eluate of the sample, wherein the total immunoglobulin concentration is scored based on detection of a low immunoglobulin concentration, a medium immunoglobulin concentration, or a high immunoglobulin concentration, and the low immunoglobulin concentration is defined as a concentration less than 1:16 titer and is assigned zero points on the relative hemolytic index, the medium immunoglobulin concentration is defined as a concentration range greater than 1:16 titer and less than 1:64 titer and is assigned 2 points on the relative hemolytic index, and the high immunoglobulin concentration is defined as a concentration greater than 1:64 titer and is assigned 10 points on the relative hemolytic index;

measuring the antibody isotype of the immunoglobulins in the sample or absorbed eluate of the sample, wherein the immunoglobulin isotype is scored based on a presence of IgM, IgG1, IgG2, IgG3, or IgG4, and the presence of IgM is assigned 10 points on the relative hemolytic index, the presence of IgG1 is assigned 10 points on the relative hemolytic index, the presence of IgG2 is assigned 5 points on the relative hemolytic index, the presence of IgG3 is assigned 10 points on the relative hemolytic index, and the presence of IgG4 is assigned zero points on the relative hemolytic index;

measuring the Fc gamma receptor affinity of the immunoglobulins in the sample or absorbed eluate of the sample, wherein the Fc gamma receptor affinity is scored based on detection of a Fcγ RI binding, a Fcγ RII binding, and/or a Fcγ RIII binding and detection of the Fcγ RI binding is assigned 10 points on the relative hemolytic index, detection of the Fcv RII binding is assigned 2 points on the relative hemolytic index, and detection of the Fcv RIII binding is assigned 5 points on the relative hemolytic index;

measuring the C1q binding capacity of the immunoglobulins in the sample or absorbed eluate of the sample, wherein C1q binding capacity is scored based on detection of a low C1q binding (less than 0.49) or a high C1q binding (0.5 or higher), and the low C1q binding is assigned 2 points on the relative hemolytic index and the high C1q binding is assigned 10 points on the relative hemolytic index; and calculating the relative hemolytic index based on said measurements of total immunoglobulin concentration, antibody isotype of the immunoglobulins, Fc gamma receptor affinity of the immunoglobulins, and C1q binding capacity of the immunoglobulins and thereby determining the risk of post-transfusion wherein the relative hemolytic index is the sum of total points accrued hemolysis for said patient.

2. The method of claim 1 wherein the relative hemolytic index of about 30 or higher indicates a high risk of intravascular hemolysis.

3. The method of claim 1 wherein the relative hemolytic index of about 15 to 30 indicates a moderate risk of intravascular hemolysis.

4. The method of claim 1 wherein the relative hemolytic index of about 15 or lower indicates a low risk of intravascular hemolysis.

5. An assay for predicting the risk of hemolysis in a patient as a result of a blood transfusion comprising measuring:
  (i) the total immunoglobulin concentration of a sample of serum, plasma or absorbed eluate of the sample, wherein the total immunoglobulin concentration is scored based on detection of a low immunoglobulin concentration, a medium immunoglobulin concentration, or a high immunoglobulin concentration, and the low immunoglobulin concentration is defined as a concentration less than 1:16 titer and is assigned zero points on the relative hemolytic index, the medium immunoglobulin concentration is defined as a concentration range greater than 1:16 titer and less than 1:64 titer and is assigned 2 points on the relative hemolytic index, and the high immunoglobulin concentration is defined as a concentration greater than 1:64 titer and is assigned 10 points on the relative hemolytic index,
  (ii) the isotype of the immunoglobulins in the sample, wherein the immunoglobulin isotype is scored based on a presence of IgM, IgG1, IgG2, IgG3, or IgG4, and the presence of IgM is assigned 10 points on the relative hemolytic index, the presence of IgG1 is assigned 10 points on the relative hemolytic index, the presence of IgG2 is assigned 5 points on the relative hemolytic index, the presence of IgG3 is assigned 10 points on the relative hemolytic index, and the presence of IgG4 is assigned zero points on the relative hemolytic index,
  (iv) the Fc gamma receptor affinity of the immunoglobulins in the sample, wherein determination of the Fc gamma receptor affinity is scored based on detection of a Fcγ RI binding, a Fcγ RII binding, and/or a Fcγ RIII binding and detection of the Fcγ RI binding is assigned 10 points on the relative hemolytic index, detection of the Fcγ RII binding is assigned 2 points on the relative hemolytic index, and detection of the Fcγ RIII binding is assigned 5 points on the relative hemolytic index, and
  (iv) the C1q complement binding capacity of the immunoglobulins in the sample, wherein C1q binding capacity is scored based on detection of a low C1q binding (less than 0.49) or a high C1q binding (0.5 or higher), and the low C1q binding is assigned 2 points on the relative hemolytic index and the high C1q binding is assigned 10 points on the relative hemolytic index; and calculating a relative hemolytic index based on said measurements of total immunoglobulin concentration, antibody isotype of the immunoglobulins, Fc gamma receptor affinity of the immunoglobulins, and C1q binding capacity of the immunoglobulins, wherein the relative hemolytic index predicts the risk of post-transfusion hemolysis in the patient wherein the relative hemolytic index is the sum of total points accrued.

6. The assay of claim 5 wherein the relative hemolytic index is calculated using a specific algorithm.

7. The assay of claim 5 wherein the relative hemolytic index of about 30 or higher indicates a high risk.

8. The assay of claim 5 wherein the relative hemolytic index of about 15 to 30 indicates a moderate risk.

9. The assay of claim 5 wherein the relative hemolytic index of about 15 or lower indicates a low risk.

10. The assay of claim 5 wherein the sample is whole blood, serum, plasma, or an eluate.

11. The assay of claim 5 wherein sample comprises an absorbed eluate of plasma or serum from said patient.

12. The assay of claim 5 wherein the immunoglobulin concentration is an immunoglobulin titer.

* * * * *